United States Patent
Larsen

(10) Patent No.: US 6,716,198 B2
(45) Date of Patent: *Apr. 6, 2004

(54) INJECTION DEVICE

(75) Inventor: Andre Larsen, Dragør (DK)

(73) Assignee: Novo Nordisk A/S, Bagsvaerd (DK)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 25 days.

(21) Appl. No.: 09/853,818

(22) Filed: May 11, 2001

(65) Prior Publication Data

US 2001/0053893 A1 Dec. 20, 2001

Related U.S. Application Data

(60) Provisional application No. 60/208,211, filed on May 31, 2000.

(30) Foreign Application Priority Data

May 18, 2000 (DK) .......................... 2000 00800

(51) Int. Cl.⁷ .......................... A61M 5/00; A61M 37/00
(52) U.S. Cl. .................. 604/207; 604/131; 222/309
(58) Field of Search ................. 604/131, 132, 604/133, 134, 207–209, 211, 108, 181, 187; 222/309, 310

(56) References Cited

U.S. PATENT DOCUMENTS

| 5,370,629 A | 12/1994 | Michel et al. |
| 5,423,757 A | 6/1995 | Olovson et al. |
| 5,624,408 A | 4/1997 | Helldin |
| 5,626,566 A | * 5/1997 | Petersen et al. ............ 604/208 |
| 5,876,377 A | * 3/1999 | Kriesel ....................... 604/132 |
| 5,961,495 A | * 10/1999 | Walters et al. .............. 604/208 |
| 6,063,059 A | 5/2000 | Kriesel |
| 6,099,504 A | 8/2000 | Gross et al. |

FOREIGN PATENT DOCUMENTS

| EP | 462 508 | 12/1991 |
| EP | 594 349 | 4/1994 |
| EP | 666 084 | 8/1995 |
| WO | WO 94/13343 | 6/1994 |
| WO | WO 96/39214 | 12/1996 |

* cited by examiner

Primary Examiner—Brian L. Casler
Assistant Examiner—Matthew F DeSanto
(74) Attorney, Agent, or Firm—Reza Green, Esq.; Richard W. Bost, Esq.; Marc A. Began, Esq.

(57) ABSTRACT

An injection device for injecting set doses from an ampoule (2) mounted in the device, which doses are set by operation of a dose setting button (7) by which operation elastic torsion rods (14) positioned parallel with the longitudinal axis of the device are twisted. By the dose setting a torque is transmitted from the dose setting button (7) to the rods (14) through gear transmissions comprising a toothing (11) carried by a tubular (8) part coupled to the dose setting button (7) to rotate with this button. The toothing (11) engages pinions (13) fixed to the proximal ends of the torsion rods (14), which are made from a super elastic material, which can stand a deformation larger than 2% without being permanently deformed.

12 Claims, 3 Drawing Sheets

INJECTION DEVICE

CROSS REFERENCE TO RELATED APPLICATIONS

This application claims the benefit of priority under 35 USC §119 Provisional Application No. 60/208,211, filed May 31, 2000 and Danish Application No. PA 2000 00900, filed May 18, 2002; the contents of both are fully incorporated by reference.

BACKGROUND OF THE INVENTION

The invention relates to injection devices for injecting set doses from an ampoule mounted in the device, which doses are set by operation of a dose setting button by which operation an elastic member is deformed to store an amount of energy which can be released to inject the set dose.

Syringes are known in which a helical spring is compressed to store energy sufficient both for automatic insertion of a needle into the skin of a user and for injection of a set dose through the inserted needle. As the force delivered by such a spring is proportional with the compression and the first part of the expansion when the spring is released is used for insertion of the needle whereas the later part of the expansion is used for the injection of the set dose from the ampoule, the characteristic of the spring must be chosen as a compromise which allow both functions.

In U.S. Pat. No. 5,320,609 separate coil springs are used for the two purposes so that each spring can be chose with the characteristic which is best for its purpose. A dose setting mechanism is so designed that setting of a dose results in a compression of the injection spring which compression can be released to perform the injection. A sequencing mechanism takes care that the injection is not made until the needle has been inserted into the skin of the user by decompression of the needle insertion spring.

Apparatuses are known which uses the same helical spring for both the needle insertion and the injection of medicine but benefits from the fact that a coil spring has different characteristics depending on the way it is used either as a source of an axial force provided by axial compression of the spring or as a source of a torque provided by rotating one end of the coil relative to the other about the longitudinal axis of the coil.

In both the above mentioned devices the characteristics of the injection springs are such that the spring force increases proportionally with the deformation so that the injection pressure will be initially be high and then fade out during the injection.

In U.S. Pat. No. 5,478,316 is described a device in which a constant force spring is provided for exertion of the injection force on the piston. The spring has the shape of a rolled up strip and the spring force is provided as the strip seeks to roll up on the roll again.

All the springs mentioned changes their dimensions during use as one part of the spring is moved relative to the other. By coil springs the ends of the coil is pressed towards each other and space must be made for the expansion of the spring. When the ends of the coil spring are rotated relative to each other the diameter of the coil changes and space must be made to allow such changes. By the constant force spring described the spring strip roll is moved relative to the end drawn off the roll and space must be made for this movement. The syringe housing must encompass all the space mentioned and this way said space contributes to an enlargement of the dimensions of the syringe. As slim syringes are aimed at, it may be seen as a way to enable minimising of a syringe if the space needed for the function of an injection spring is minimised.

SUMMARY OF THE INVENTION

According to the invention an injection device as described in the opening of this application is characterised in that the elastic member is a torsion rod which is twisted by the operation of the dose setting member.

The torsion rod may be placed parallel with the longitudinal axis of the syringe with its distal end fixed relative to the syringe housing, and the toque may be transmitted from the dose setting button to the proximal end of the rod by a gear transmission.

The gear transmission may appropriately be established by a toothing carried by the dose setting member to rotate with this member, which toothing engage a gear wheel fixed to the proximal end of the torsion rod. The toothing carried by the dose setting member may appropriately have a larger diameter than has the gear wheel at the proximal end of the rod.

In the following the invention is described in further details with reference to the drawing, wherein

BRIEF DESCRITPION OF THE DRAWINGS

FIG. 1 schematically show a sectional view of a syringe provided with torsion rods according to the invention.

DETAILED DESCRIPTION OF THE INVENTION

Figure 1:
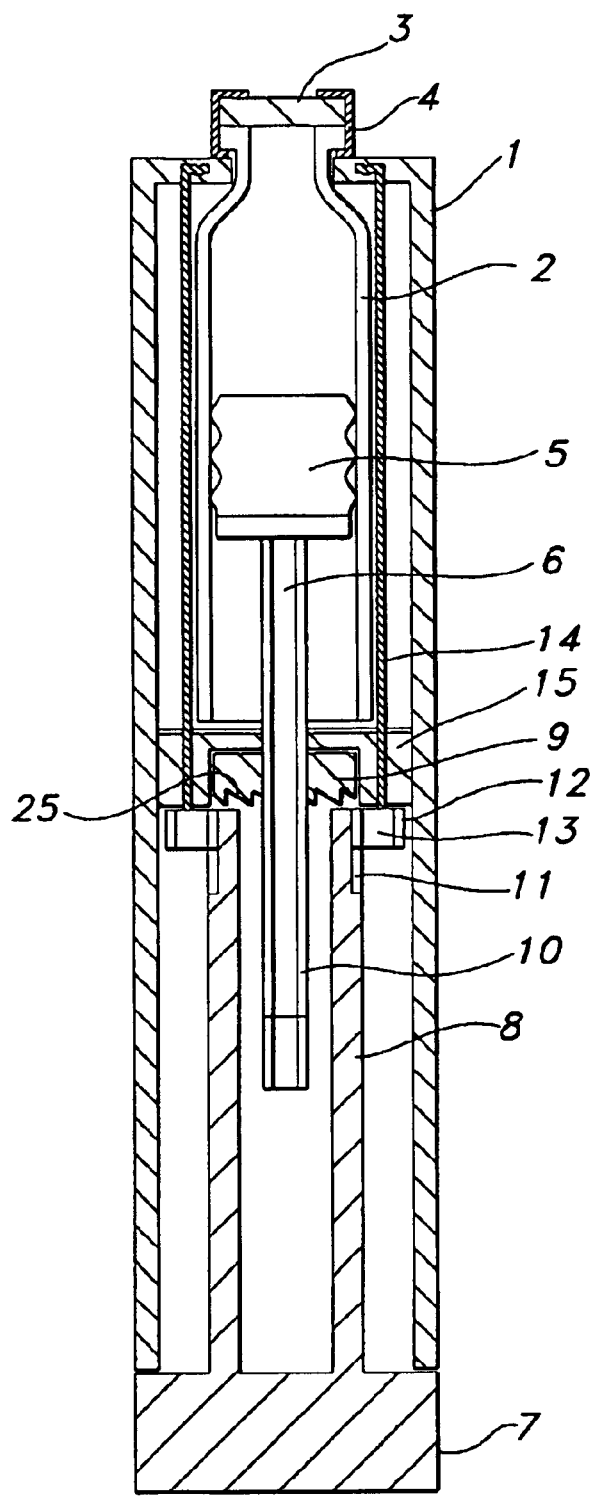
Figure 2:
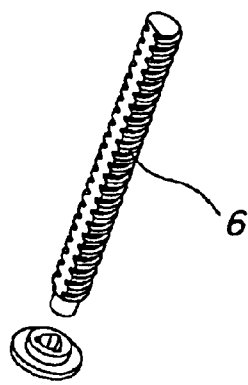
FIG. 2 shows a threaded piston rod and nut for use with the present invention.

The syringe comprises a housing 1 accomodating an ampoule 2 which is at a distal end closed by a rubber membrane 3 sealingly held against a flange by a metal cap 4 at said distal end of the ampoule 2. A not shown needle hub with a needle can be mounted onto the syringe so that one end of the needle penetrates the rubber membrane to communicate with a medicament contained in the ampoule whereas the other end of the needle can be inserted into the skin of a person, who is going to receive an injection.

A piston 5 closing the proximal end of the ampoule 2 can be pressed further into the ampoule by a piston rod 6 to eject a portion of the content of the ampoule through the said needle. The size of the portion can be set by rotating a dose setting member 7 in a clockwise direction over an angle corresponding to the dose one wants to set, which dose is consecutively injected by rotating back the dose setting member 7 to its original position.

Figure 3:
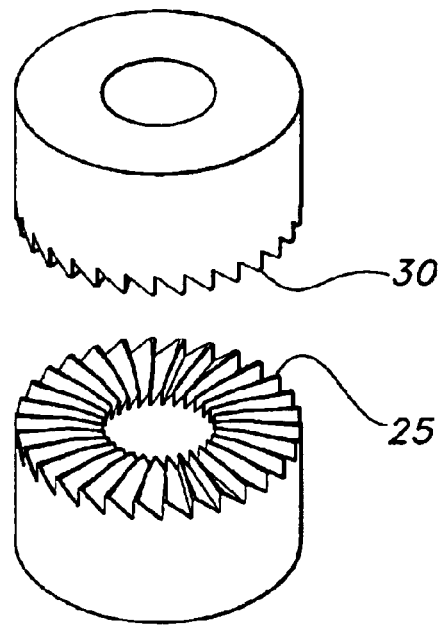
FIG. 3 shows a unidirectional coupling.

The dose setting member is provided with a tubular part 8 which has at its distal end a toothed rosette 25 cooperating with a corresponding rosette 25 (See FIG. 3) on a driver nut 9 o that during the clockwise rotation of the dose setting member, the saw teeth of the dose setting member rides over the saw teeth of the driver nut 9, whereas during the anticlockwise rotation of the dose setting member 7 the teeth of this member engages the teeth of the driver nut 9 to rotate this nut.

The nut 9 has an inner thread engaging an outer thread 10 on the piston rod 6. The nut is rotatable but not lengthwise displaceable in the housing 1 and consequently rotation of the nut 9 will cause the piston rod 6 to move in its longitudinal direction as this rod is not rotatable but longitudinal displaceable. The toothings of driver the nut and of the part 8 of the dose setting member 7 forms a unidirectional coupling which allows the nut to be driven in a direction which causes the piston rod 6 to be moved further into the ampoule when the dosing member is returned to its original rotational position. This is a common construction for injection devices by which a dose can be set and subsequently injected.

In the device according to the invention the tubular part 8 of the dose setting member 7 is at its distal end along its perimeter provided with gear teeth 11 to form a gear which is engaged by the teeth 12 of a pinion 13 which is mounted at a proximal end of a torsion rod 14 the distal end of which is moulded into the housing 1 or in another way fixed to that housing. Adjacent to the pinion 13 the torsion rod is supported by a member 15 which further has a not round central opening through which the piston rod 6 having a similar not round cross section fits. The member 15 is fixed to the housing 1.

When a dose is set by clockwise rotation of the dose-setting member 7, the toothing on the tubular part 8 will drive the pinion 13 whereby the proximal end of the torsion rod 14 is rotated relative to the distal end of this rod. Thereby a spring force is stored in the torsion rod 14 which spring force will try to rotate said proximal end back to its original position. When a dose is set energy is stored in the torsion rod 14 which energy can be used to perform the rotation of the nut 9, which is necessary to inject the set dose.

Figure 4:
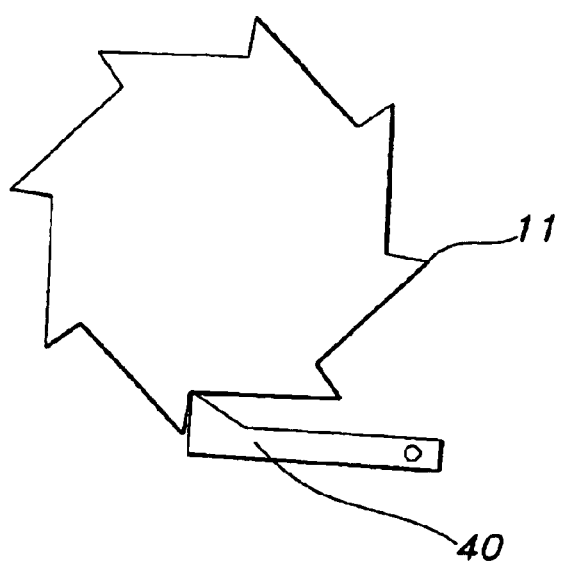
FIG. 4 shows a pawl and ratchet mechanism for use with the present invention.

A pawl mechanism 40 (See FIG. 4) can be provided, which keeps the dose setting member 7 in its position when it is rotated to set a dose. If it not for the pawl 40, the spring force of the torsion rod would immediately rotate the member 7 back and inject the set dose. Now the dose can be set before the needle is inserted into the skin of the person who is going to receive the injection, when the pawl is thereafter released, the torsion rod will via the pinion 13, the tubular part 8, and the unidirectional coupling between the tubular part 8 and the nut 9 drive the nut to advance the piston rod into the ampoule to inject the set dose.

A not shown pawl mechanism can be provided, which keeps the dose setting member 7 in its position when it is rotated to set a dose. Was it not for the pawl, the spring force of the torsion rod would immediately rotate the member 7 back and inject the set dose. Now the dose can be set before the needle is inserted into the skin of the person who is going to receive the injection, and when the pawl is thereafter released, the torsion rod will via the pinion 13, the tubular part 8, and the unidirectional coupling between the this tubular part 8 and the nut 9 drive this nut to advance the piston rod into the ampoule to inject the set dose.

In the device shown in FIG. 1 two torsion rods are shown, each with a pinion engaging the toothing 11 of the tubular part 8 of the dose setting member 7. The device must comprise at least one torsion rod, but if wanted it can comprise two or more torsion rods which are positioned parallel with the longitudinal axis of the ampoule distributed along the perimeter of this ampoule.

The gear toothing on the tubular part 8 can be provided closer to the distal end of this part. This will allow the use of longer torsion rods. The torsion rods can be supported in longitudinal channels in the housing and they may be made of a super elastic material, i.e. a material which allows a deformation larger than 2% without being permanently deformed, which will allow a heavier winding of the rods. Further the rods can be pre-stressed so that they posses some stored spring energy even before they are wound due to the dose setting. This will ensure a safe return of the dose setting member 7 to its original position which must be defined by a stop to avoid that the member 7 is rotated further backward than to its original position.

What is claimed is:

1. A medication delivery device comprising:
   a housing having a compartment for mounting a medication cartridge having a moveable piston;
   a dose setting mechanism for setting a desired dose, the dose setting mechanism having a rotateable dose setting element having a tubular element with a cylindrical axis of rotation;
   a threaded piston rod for abutting an piston in an ampoule cartridge;
   a pinion that is coupled to the tubular element of the dose setting mechanism;
   a means for coupling the pinion to a drive nut, the drive nut being rotateable but not linearly displaceable; and
   a rotateably displaceable elastic energy storing torsion rod for storing a rotational force, the energy storing torsion rod having a first end connected to the pinion and a second end connected to the housing; the torsion rod having sufficient stiffness to store sufficient force to drive the drive nut, thereby causing linear displacement of the piston rod and expelling a dose from the medication cartridge; wherein the torsion rod comprises a super elastic material, which can withstand an elastic deformation greater the 2%.

2. The medication delivery device of claim 1, wherein the device further comprises a transmission coupling the torsion rod(s) to the dose setting element.

3. The medication delivery device of claim 2, wherein the transmission is a gear transmission.

4. The medication delivery device of claim 1, wherein the first end(s) of the torsion rod(s) are connected at a distal end of the housing and the dose setting element is located at a proximal end of the housing and wherein the tubular element extends distally from the dose setting element.

5. The medication delivery device of claim 1, wherein the torsion rod(s) are parallel to the tubular dose setting element and are pre-stressed.

6. A medication delivery device comprising:
   a housing;
   a rotatable dose setting element having an axis of rotation;
   one or more rotateably displaceable elastic energy storing torsion rod(s) coupled to the rotateable dose setting element, the torsional rod(s) each having a first end and a second end, the first end(s) irrotatably connected to the housing so that the first end cannot rotate with respect to the housing and the second end(s) coupled to the the rotatable dose setting element at the second end of the torsional energy storing rod(s), thereby allowing rotational displacement of the second rod end(s) relative to the first rod end(s) when the dose setting member is rotated and thereby storing rotational energy in the torsion rod(s), the torsion rods being generally parallel to the axis of rotation of the rotatable dose setting element.

7. The medication delivery device of claim 6, further comprising:
   a releaseable locking means for locking the torsion rod(s) in a rotationally displaced position, relative to the first end, thereby allowing energy to be stored in the torsion rod(s) for later use.

8. The medication delivery device of claim 7, wherein the dose setting element has a tubular element and the torsional rod(s) are prestressed and then coupled to the tubular element.

9. The medication delivery device of claim 8, wherein a transmission comprising one or more gears couples dose setting element to the torsional rod(s).

10. A medication delivery device comprising:

a housing;

a linearly displaceable piston rod;

a rotatable mechanical piston rod drive, the drive being coupled to the piston rod so that rotation of the drive linearly displaces the piston rod;

an energy storage device for storing a rotational force for rotating the mechanical piston rod drive to linearly displace the piston rod, the energy storage device comprising one or more super elastic linear torsion rods, which can withstand an elastic deformation greater than 2% and wherein the torsion rods having a first end irrotatably fixed to the housing and a second end coupled to the drive, the second end being rotationally displaceable relative to the first end to store a rotational force.

11. The medication delivery device of claim 10, further comprising a releaseable ratchet means for locking the second end of the torsion rods in a rotationally displaced position, thereby allowing storage of a rotational force necessary to drive the piston rod drive until a time when it is desirable to drive the piston rod drive with hat linearly displacing the piston rod.

12. The medication 10, wherein the device is assembled with the torsion rods pre-stressed.

* * * * *

UNITED STATES PATENT AND TRADEMARK OFFICE
CERTIFICATE OF CORRECTION

PATENT NO. : 6,716,198 B2 Page 1 of 1
APPLICATION NO. : 09/853818
DATED : April 6, 2004
INVENTOR(S) : Andre Larsen It is certified that error appears in the above-identified patent and that said Letters Patent is hereby corrected as shown below:

Claim 11

Column 6, Line 13

Change "hat" to --that--

Signed and Sealed this

Eighteenth Day of September, 2007

JON W. DUDAS
*Director of the United States Patent and Trademark Office*